United States Patent
Campbell et al.

(10) Patent No.: US 6,670,513 B1
(45) Date of Patent: Dec. 30, 2003

(54) PROCESS FOR PRODUCING ALKYLATED HYDROXYL-CONTAINING AROMATIC COMPOUNDS

(75) Inventors: Curtis Bay Campbell, Hercules, CA (US); Jean Louis Le Coënt, Le Havre (FR)

(73) Assignees: Chevron Oronite Company, LLC, San Francisco, CA (US); Chevron Oronite S.A., Levallois-Perret (FR)

( * ) Notice: Subject to any disclaimer, the term of this patent is extended or adjusted under 35 U.S.C. 154(b) by 0 days.

(21) Appl. No.: 09/454,785

(22) Filed: Dec. 3, 1999

(51) Int. Cl.⁷ .............................................. C07C 37/00
(52) U.S. Cl. .................. 568/793; 568/766; 568/785; 568/786; 568/788; 568/790; 568/791; 568/793
(58) Field of Search ................. 568/766, 788, 568/785, 790, 793, 786, 791

(56) References Cited

U.S. PATENT DOCUMENTS

| | | | |
|---|---|---|---|
| 2,404,340 A | | 7/1946 | Zimmerman ................ 260/671 |
| 3,422,157 A | * | 1/1969 | Kaufman .................... 568/788 |
| 3,932,537 A | | 1/1976 | Wetzel et al. ........... 260/624 C |
| 4,168,390 A | * | 9/1979 | Alfs ............................ 568/788 |
| 4,198,531 A | * | 4/1980 | Merger ....................... 568/788 |
| 4,202,199 A | * | 5/1980 | Merger ....................... 568/788 |
| 4,632,771 A | * | 12/1986 | Liston ........................ 568/766 |
| 4,643,838 A | * | 2/1987 | Liston ........................ 568/766 |
| 4,914,246 A | | 4/1990 | Oswald et al. ............. 568/793 |
| 4,973,764 A | * | 11/1990 | Oswald ...................... 568/788 |
| 5,087,793 A | * | 2/1992 | Akiyama .................... 585/666 |
| 5,208,390 A | * | 5/1993 | Onopchenko ............... 568/766 |
| 5,243,115 A | * | 9/1993 | Smith, Jr. ................... 585/446 |
| 5,320,762 A | * | 6/1994 | Campbell ..................... 252/25 |
| 5,510,306 A | * | 4/1996 | Murray ....................... 585/666 |
| 5,523,510 A | * | 6/1996 | Pellet et al. ................ 585/671 |
| 5,589,442 A | | 12/1996 | Gee et al. ................... 507/103 |
| 5,741,759 A | * | 4/1998 | Gee ............................ 507/103 |
| 5,922,922 A | * | 7/1999 | Harris ........................ 585/323 |
| 5,986,157 A | * | 11/1999 | Ryu ............................ 585/671 |

FOREIGN PATENT DOCUMENTS

EP 807616 A * 11/1997

* cited by examiner

*Primary Examiner*—Michael L. Shippen
(74) *Attorney, Agent, or Firm*—Richard J. Sheridan; Josetta I. Jones; Martin C. Fallon

(57) ABSTRACT

An alkylated hydroxyl-containing aromatic compound is produced by isomerizing a normal alpha-olefin having from about 16 to about 30 carbon atoms in the presence of a first solid, acidic catalyst capable of inducing both olefin isomerization and skeletal isomerization to produce a mixture of isomerized olefin, then alkylating an hydroxyl-containing aromatic compound with the mixture of isomerized olefins in the presence of a second solid, acidic catalyst. The first solid, acidic catalyst can be SM-3, MAPO-11, SAPO-11, SSZ-32, ZSM-23, MAPO-39, SAPO-39, ZSM-22, SSZ-20, ZSM-35, SUZ-4, NU-23, NU-87, natural ferrierite or synthetic ferrierite. The second solid, acidic catalyst can be a sulfonic acid anionic ion exchange resin catalyst or an acidic clay.

27 Claims, No Drawings

PROCESS FOR PRODUCING ALKYLATED HYDROXYL-CONTAINING AROMATIC COMPOUNDS

The present invention relates to a process for alkylation of an aromatic compound having at least one hydroxyl group on the aromatic ring, such as phenol, catechol, anisole, cresol, resorcinol or mixtures thereof, to provide an aromatic product having both hydroxyl and alkyl groups on the same aromatic ring in which the content of the para-alkyl isomer is high. The alkylated products are useful in making detergents for lubricating oils.

SUMMARY OF THE INVENTION

In accordance with the present invention, there is provided a process for producing alkylated, hydroxyl-containing aromatic compounds, said process comprising:

(a) isomerizing a normal alpha-olefin or mixture of normal alpha-olefins having from about 16 to about 30 carbon atoms in the presence of a first acidic catalyst capable of inducing both olefin isomerization and skeletal isomerization to produce a mixture of isomerized olefins;

(b) alkylating a hydroxyl-containing aromatic compound with said mixture of isomerized olefins in the presence of a second acidic catalyst comprising a sulfonic acid resin catalyst or an acidic clay.

Also provided in accordance with this invention is a process for producing an alkylated hydroxyl-containing aromatic compound, said process comprising:

(a) isomerizing a normal alpha-olefin or mixture of normal alpha-olefins having from about 16 to about 30 carbon atoms in the presence of a first acidic catalyst capable of inducing both olefin isomerization and skeletal isomerization to produce a mixture of straight-chain and branched-chain isomerized olefins;

(b) alkylating an hydroxyl-containing aromatic compound selected from the group consisting of phenol, catechol, anisole, cresol, resorcinol and mixtures thereof with said mixture of isomerized olefins in the presence of a second solid, acidic catalyst comprising a sulfonic acid resin catalyst or an acidic clay.

Among other factors, the present invention is based on the discovery that olefin and skeletal isomerization of the normal alpha-olefin prior to alkylation of the hydroxyl-containing aromatic compound results in an alkylated product containing a high content of compounds in which the alkyl and hydroxyl groups are in the para position relative to each other.

DETAILED DESCRIPTION OF THE INVENTION

In its broadest aspect, the present invention involves a process for producing alkylated aromatic compounds that have at least one hydroxyl and at least one alkyl group on the same aromatic ring. That process comprises isomerizing a normal alpha-olefin or mixture of normal alpha-olefins (referred to herein collectively as "NAO") having from about 16 to about 30 carbon atoms in the presence of a first solid, acidic catalyst capable of inducing both olefin isomerization and skeletal isomerization to produce a mixture of isomerized olefins, then alkylating an aromatic compound having at least one hydroxyl group on the aromatic ring with the mixture of isomerized olefins in the presence of a second solid, acidic catalyst comprising a sulfonic acid resin catalyst or an acidic clay.

The alkylation of phenol with olefins, under normal alkylation conditions using a macroporous sulfonic acid resin catalyst or acidic clay, nominally affords an alkylated phenol product in which the para and ortho isomers are dominant. When one uses a normal alpha-olefin to alkylate the phenol, the para isomer/ortho isomer ratio content is only about 50/50.

It has now been discovered that by isomerizing an NAO prior to using it to alkylate phenol (or other hydroxyl-containing aromatic compounds), a significant increase in the para isomer is obtained in the alkylated product, e.g., the para isomer/ortho isomer ratio can be increased to about 80/20. The alkylated product can be used to prepare detergents for lubricating oil, and the high para-isomer content allows more base to be added to the detergent.

AROMATIC COMPOUNDS CONTAINING AT LEAST ONE HYDROXYL GROUP ON THE AROMATIC RING

The hydroxyl-containing aromatic compounds that are alkylated in the subject process include phenol, catechol, anisole, cresol, resorcinol and mixtures thereof, with phenol being the preferred compound.

NORMAL ALPHA-OLEFINS

The normal alpha-olefins that are isomerized prior to the alkylation of the hydroxyl-containing aromatic compounds are normal alpha-olefins or mixtures of normal alpha-olefins that have from about 16 to about 30 carbon atoms per molecule. Preferably, they have about 20 to about 28 carbon atoms per molecule.

OLEFIN ISOMERIZATION CATALYST

The catalyst used to isomerize the normal alpha-olefin or mixture of normal alpha-olefins can be any catalyst that is capable of inducing both olefin isomerization and skeletal isomerization in the NAO while leaving the NAO otherwise essentially in tact. As used herein, the term "olefin isomerization" refers to movement of the carbon-carbon double bond within the molecule, and the term "skeletal isomerization" refers to rearrangement of the carbon atoms within the molecule. Examples of such catalysts include solid, acidic catalysts comprising at least one metal oxide, and having an average pore size of less than 5.5 Angstroms. Preferably, the solid, acidic catalyst comprises a molecular sieve with a one-dimensional pore system. More preferably, it is selected from the group consisting of molecular sieves SM-3, MAPO-11, SAPO-11, SSZ-32, ZSM-23, MAPO-39, SAPO-39, ZSM-22, and SSZ-20. The preferred molecular sieves are SAPO-11 and SSZ-32. Other possible solid, acidic catalysts useful for isomerization include molecular sieves ZSM-35, SUZ4, NU-23, NU-87, and natural or synthetic ferrierites. These molecular sieves are well known in the art and are discussed in Rosemarie Szostak's Handbook of Molecular Sieves (New York, Van Nostrand Reinhold, 1992), and U.S. Pat. No. 5,282,958, issued Feb. 1, 1994 to Santilli et al., both of which are hereby incorporated by reference.

The catalyst can be an admixture with at least one Group VIII metal. Preferably, the Group. VIII metal is selected from the group consisting of at least one of platinum and palladium, and optionally other catalytically active metals such as molybdenum, nickel, vanadium, tungsten, cobalt, zinc and mixtures thereof. More preferably, the Group VIII metal is selected from the group consisting of at least one of platinum and palladium. The amount of metal ranges from about 0.01% to about 10% by weight of the catalyst (not counting the weight of the metal), preferably from about 0.2% to about 5% by weight of the catalyst. The techniques of introducing catalytically active metals to the catalyst are disclosed in the literature, and pre-existing metal incorporation techniques and treatment of the catalyst to form an active catalyst such as ion exchange, impregnation or occlusion during preparation of the catalyst are suitable. Such techniques are disclosed in U.S. Pat. Nos. 3,236,761; 3,226,339; 3,236,762; 3,620,960; 3,373,109; 4,202,996; 4,440,996 and 4,710,485 which are incorporated herein by reference.

The "metal" or "active metal" as used herein means one or more metals in the elemental state or in some form such as sulfide, oxide or mixtures thereof. Regardless of the state in which the metallic component actually exists, the concentrations are computed as if they existed in the elemental state.

The catalyst is used in an amount effective to catalyze the isomerization reaction.

OLEFIN ISOMERIZATION PROCESS CONDITIONS

A preferred method of isomerizing the normal alpha-olefin or mixture of normal alpha-olefins involves catalytic isomerization using, for instance, a platinum-supported-on-SAPO-11 molecular sieve catalyst to partially isomerize a feed containing the NAO. This and related catalysts are described in U.S. Pat. No. 5,082,986, issued Jan. 21, 1992 to Miller, which is hereby incorporated by reference.

For platinum-on-SAPO-11 catalysts, partial isomerization is preferred. Therefore, preferred operating conditions include weight hourly space velocities (WHSV) between about 0.5 and about 10 at temperatures between about 100° C. and about 250° C. More preferred conditions include WHSV's of between about 0.5 and about 5 at temperatures of about 120° C. to about 160° C.; most preferred conditions include WHSV's of between about 0.5 and about 3.5 at temperatures of about 120° C. to about 140° C. Lower temperatures result in substantial olefin double bond migration, while higher temperatures result in increased skeletal rearrangement. The process is preferably conducted in the presence of added hydrogen.

The isomerized olefins contain branched-chain olefins. The branching may occur at a carbon atom that is part of the carbon-carbon double or at a carbon atom that does not form part of the double bond. Examples of the branched-chain olefins include, but are not limited to, the following:

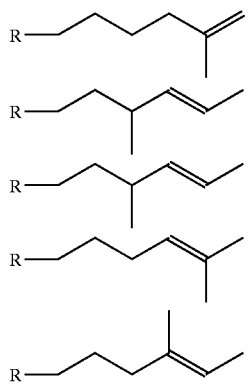

where R is the remainder of the olefin. Preferably, at least 70% of the isomerized olefins are branched, more preferably at least 90%. It has also been found that the more vinylidene and tri-substituted olefin isomers there are in the isomerized olefin mixture, the higher the para/ortho ratio will be in the alkylated product.

ALKYLATION CATALYST

The second acidic catalyst is a solid catalyst comprising a sulfonic acid resin catalyst or an acidic clay. The sulfonic acid resin catalyst is an anionic ion exchange resin such as Amberlyst 15 and Amberlyst 36 sulfonic acid ion exchange resins sold by Rohm and Haas Co. Acidic clays such as Filtrol-24 can also be used. The catalyst is employed in an amount sufficient to catalyze the alkylation of the hydroxyl-containing aromatic compound. Typically, the amount of catalyst used will be about 1 wt. % to about 20 wt. %, based on the weight of the hydroxyl-containing aromatic compound.

ALKYLATION PROCESS CONDITIONS

The alkylation reaction is typically carried out with an hydroxyl-containing aromatic compound or mixture of hydroxyl-containing compounds and a mixture of isomerized olefins in hydroxyl-containing aromatic compound:isomerized olefin molar ratios from 1:15 to 25:1. Process temperatures can range from about 90° C. to about 150° C. Since the olefins have a high boiling point, the process is preferably carried out in the liquid phase. The alkylation process may be carried out in batch or continuous mode. In the batch mode, a typical method is to use a stirred autoclave or glass flask which may be heated to the desired reaction temperature. A continuous process is most efficiently carried out in a fixed bed process. Space rates in a fixed bed process can range from about 0.01 to about 10 or more WHSV.

In a fixed bed process the catalyst is charged to the reactor and activated or dried at a temperature of at least 100° C. under vacuum or flowing inert, dry gas. After activation, the catalyst is cooled to ambient temperature and a flow of the hydroxyl-containing aromatic compound is introduced. Optionally, the hydroxyl-containing aromatic compound may be added to the catalyst at the reaction temperature. A flow of the isomerized olefin is then mixed with the hydroxyl-containing aromatic compound and allowed to flow over the catalyst. The reactor effluent containing alkylate product and excess hydroxyl-containing aromatic is collected. Excess hydroxyl-containing aromatic is then removed by distillation, stripping, evaporation under vacuum, or other means known to those skilled in the art.

EXAMPLES

The invention will be further illustrated by the following examples, which set forth particularly advantageous embodiments. While the Examples are provided to illustrate the present invention, they are not intended to limit it.

Example 1

Pre-isomerization of $C_{20-24}$ Normal Alpha Olefin—Flow Reactor $C_{20-24}$ Normal Alpha Olefin (composed of 89.1% alpha-olefin, 0.5% beta-olefin, 1.4% internal-olefin, 0.2%, tri-substituted olefin and 9.5% vinylidene-olefin by carbon NMR and 11% branching by IR was pumped up-flow through a fixed bed reactor (83.8 cm high by 22.6 mm ID) containing 216 gms of SAPO-11 catalyst (⅛" extrudate) sandwiched between 126.5 gms of Alundum (100 mesh) at each end of the reactor operating isothermally at various temperatures and WHSV's. Samples were collected at the operating temperatures and WHSV's shown in the table below.

| Average Reactor Temperature (° C.) | Average WHSV (hr$^{-1}$) | % Alpha-olefin | % Beta-olefin | % Internal olefin | % Tri-Substituted olefin | % Vinylidene olefin |
|---|---|---|---|---|---|---|
| 186 | 5.46 | 31.7 | 20.9 | 68.1 | 4.6 | 18.9 |
| 201 | 1.44 | 7.8 | 22.3 | 91.5 | 11.3 | 25.5 |
| 213 | 1.28 | 2.9 | 25.0 | 89.1 | 24.7 | 37.5 |

Procedure for Determining Olefin Distribution of Pre-isomerized Normal Alpha Olefins by Carbon Nuclear Magnetic Resonance (NMR)

A Varian Gemini NMR spectrometer operating at 3000 MHz was used to determine the olefin distribution in the pre-isomerized normal alpha olefins. A macro was written to calculate the relative percent of alpha, beta, internal, tri-substituted and vinylidene olefins present from the integration of the $^{13}$C NMR spectra (recorded in CDCl$_3$ containing a relaxation agent, Chromium (III) acetylacetonate, with a sufficient pulse delay to make the integrals more quantitative). The vinylidene olefin content was indicated as the sum of the $C_2$ and $C_4$ and higher vinylidene olefins present. The spectral regions used to determine the various olefin species present were as follows:

| Olefin Species | Description | Chemical Shift Assignment (ppm) | Integral Code |
|---|---|---|---|
| Alpha-olefin | C1 | 113.0–115.4 | C |
|  | C2 | 137.6–140.0 | I |
| Beta-olefin | C2 Z/E | 122.5–126.0 | E |
|  | C3 Z/E | 130.9–132.5 | G |
| Internal Olefin | RHC = CHR Z/E | 129.0–130.8 | F |
| Tri-substituted olefin | = CHR | 117.0–119.5 | D |
|  | = CRR | 134.0–137.5 | H |
| Vinylidene olefin | = CH2 | 106.7–108.0 | A |
|  | = CRR' Z/E | 108.1–109.6 | B |
|  |  | 149.0–150.5 | J |
|  |  | 150.6–152.0 | K |
| Total | — | — | Sum of A through K |

The percent of each olefinic species present is calculated from the integral of each region (Integral Code) above as follows:

% Alpha-olefin=((C+I)/Total)×100

% Beta-olefin=((2×G)/Total)×100

% Internal-olefin=(((2xG)+F)/Total)×100

% Tri-substituted olefin=(D+E+H−G)/Total)×100

% Vinylidene olefin=((A+K+B+J)/Total)×100

Example 2

Alkylation of Phenol With Pre-Isomerized $C_{20-24}$ Normal Alpha Olefin—General Micro-vial Batch Procedure To a 30 ml glass vial (30 ml volume Wheaton Glass Serum Bottles, 20 mm mouth) fitted with a magnetic stir bar was added 1.0 gm of Amberiyst-36 catalyst (anionic ion exchange resin from Rohm and Haas Co.) followed by 10 gms of a solution of 4.4 gms phenol (46.8 mmol) and 3.6 gms of pre-isomerized $C_{20-24}$ normal alpha olefin. The glass vial was then sealed with a cap (Wheaton Closed Top Seals with Teflon Faced Rubber Septa) using a crimping tool. The vial was then placed in a magnetically stirred oil bath at 130°±3° C. After 24 hours, the vial was removed from the oil bath and wiped with a rag to remove oil from the exterior of the glass vial. The glass vial was allowed to cool to approximately 35° C. at which time the cap was removed and 15–20 mls of hexane was added. The contents of the vial was then gravity filtered to remove the catalyst. The filtrate was washed six times with 5 ml portions of methanol/water (50/50 by volume). The organic layer was dried over anhydrous MgSO$_4$, filtered and the hexane allowed to evaporate at room temperature overnight. The resulting oil was analyzed by SFC to determine the unreacted olefin content and by IR to determine the ortho/para ratio of the product alkylphenol. Table I summarizes the properties of the pre-isomerized $C_{20-24}$ normal alpha olefins as well as one non-isomerized $C_{20-24}$ normal alpha olefin used to prepare alkylphenols.

TABLE I

| $C_{20-24}$ Alpha Olefin Sample | % Alpha-olefin | % Beta-olefin | % Internal olefin | % Tri-Substituted olefin | % Vinylidene olefin | Total % Branching |
|---|---|---|---|---|---|---|
| 1 | 25.4 | 36.8 | 68.4 | 5.9 | 0.2 | 23 |
| 2 | 3.1 | 32.3 | 90.8 | 5.8 | 0.3 | 28 |
| 3 | 89.1 | 0.5 | 1.4 | 0.2 | 9.5 |  |
| 4 | 18.2 | 27.1 | 40.3 | 41.6 | 0 | 94 |
| 5 | 7.2 | 22.0 | 43.2 | 47.5 | 2.1 | 70 |

*Not pre-isomerized $C_{20-24}$ Normal Alpha Olefin.

Table II summarizes the para-alkylphenol content and the unreacted olefin content in the alkylphenols prepared from the corresponding olefins in Table I.

TABLE II

| $C_{20-24}$ Alpha olefin sample from Table I | % Para-alkylphenol content | % Olefin Content |
|---|---|---|
| 1 | 51 | 0.5 |
| 2 | 48 | 0.1 |
| 3 | 45 | 0.2 |
| 4 | 86 | 14.0 |
| 5 | 82 | 2.7 |

Adding the % tri-substituted olefin content and the % vinylidene content for a variety of pre-isomerized $C_{20-24}$ alpha olefin samples used to alkylate phenol and plotting this summed value versus the para-alkylphenol content of the corresponding alkylphenol showed a strong linear correlation.

Procedure for Determining Percent Olefin Content of $C_{20-24}$ Alkylphenols by Supercritical Fluid Chromatography (SFC)

A Dionex Lee Scientific Model 600 supercritical fluid chromatograph (SFC) equipped with a 10 meter x 195 micron OD/50 micron ID 0.25 micron film SB-Methyl-100 capillary column, an FID detector operating at 325° C. and carbon dioxide eluent was used with time-split injection. The following density ramp program was used (isothermal oven at 100° C.):

Initial density=0.2 g/cc
Inject sample
Hold five minutes
Ramp to 0.3 g/cc at 0.02 g/cc/min
Ramp to 0.5 g/cc at 0.01 g/cc/min
Ramp to 0.76 g/cc at 0.02 g/cc/min
Hold 12 minutes For the pre-isomerized $C_{20-24}$ alkylphenols prepared and under the conditions that contribute to the relative retention times (carrier flow, condition of the column and other factors), the $C_{20-24}$ unreacted olefin eluted between 24 and 33 minutes and the alkylphenol between 33.5 and 45 minutes. The purity of the alkylphenols was calculated as follows:

$$\text{Percent olefin} = \frac{\text{Peak area between 24 and 33 minutes}}{\text{Peak area between 24 and 45 minutes}} \times 100$$

Example 3

Alkylation of Phenol With Pre-isomerized $C_{20-24}$ Normal Alpha Olefin—Large Scale Batch Procedure To a 3 liter, 3 neck round bottom flask fitted with a condenser and a mechanical stirrer was added of 1128 gms of phenol and 888 gms of a pre-isomerized $C_{20-24}$ normal alpha-olefin (composed of 18.7% alpha-olefin, 27.1% internal olefin, 27.1% beta-olefin, 41.6% tri-substituted olefin and 0% vinylidene olefin) followed by 106.6 gms of catalyst (Amberlyst-36 ion exchange resin available from Rohm and Haas Co.). This mixture was heated to 120° C. under an atmosphere of nitrogen at atmospheric pressure with stirring for 60 hours. The reaction mixture was filtered to remove the catalyst. The filtrate was distilled to remove the excess phenol (230° C. and 2mm Hg vacuum). The resulting product (880 gms) was analyzed by HPLC and found to have the following composition:

Ortho-alkylphenol=19.2%, para-alkylphenol=74.6%, phenol= <0.05%, di-alkylphenol=1.9%, ether=4.3%.

Procedure for Determining the Composition of Alkylphenol by High Performance Liquid Chromatography (HPLC)

A Spectra-Physics !sochrom HPLC was used equipped with a RheoDyne Model 71-25 injection valve with a 5 microliter injection loop, a Beckman Ultra Sphere 3 micron Cyano column (7.5 cm long by 4.6 mm ID) and a Spectra-Physics Spectra Chrom 100 UV detector (280 nm wavelength) operating isocratically with a mixture of cyclohexane/ethanol (99.75:0.25) at 40° C.

The alkylphenol sample (0.1 gm±0.02 gm) was dissolved in 5 gm of cyclohexane for analysis. Response factors were used to normalize the chromatographic peak areas of the individual components using the following equation:

$$W_i = 100 \times K_i \times A_i \Big/ \sum_{i=1}^{n} K_i \times A_i$$

Where, for n components;
$W_i$=weight of component i
$K_i$=gram-extinction coefficient for component i
$A_i$=area of the peak for component i The order of elution of the components is:
Ether, 0.45 minutes–0.65 minutes
Di-alkylphenol, 0.66 minutes–1.2 minutes
Ortho-alkylphenol, 1.21 minutes–1.8 minutes
Para-alkylphenol, 1.81 minutes–2.6 minutes
Phenol, 3.4 minutes–3.7 minutes.

Example 6

Procedure for Determining Ortho-Alkylphenol and Para-Alkylphenol by Infrared Spectroscopy (IR)

A FTIR was used. A sample of alkylphenol was placed on a salt block and the infrared spectrum recorded between 600 and 4000 cm$^{-1}$. The absorbance of the peak at 747 cm$^{-1}$ and 825 cm$^{-1}$ was measured and the ortho/para absorbance ratio calculated:

$$\text{ortho/para absorbance ratio} = \frac{\text{absorbance @747 cm}^{-1}}{\text{absorbance @ 825 cm}^{-1}}$$

Using the ortho/para absorbance ratio, the % para-alkylphenol was determined from a calibration curve of ortho/para absorbance ratio versus wt. % ortho content developed using standards.

While the present invention has been described with reference to specific embodiments, this application is intended to cover those various changes and substitutions that may be made by those skilled in the art without departing from the spirit and scope of the appended claims.

What is claimed is:

1. A process for producing alkylated, hydroxyl-containing aromatic compounds, said process containing:
   (a) isomerizing a normal alpha-olefin or mixture of normal alpha-olefins having from about 16 to about 30 carbon atoms in the presence of a first acidic catalyst capable of inducing both olefin isomerization and skeletal isomerization to produce a mixture of isomerized olefins wherein at least about 70% of the isomerized olefins are branched-chain olefins;
   (b) alkylating a hydroxyl-containing aromatic compound with said mixture of isomerized olefins in the presence of a second acidic catalyst comprising a sulfonic acid resin catalyst or acidic clay to thereby provide an alkylated hydroxyl containing aromatic compound having at least 82% of the para isomer.

2. A process according to claim 1 wherein the first acidic catalyst is a solid catalyst comprising at least one metal oxide, and having an average pore size of less than 5.5 angstroms, and wherein the isomerized olefin is a mixture of straight-chain and branched-chain olefins.

3. A process according to claim 2 wherein the first solid, acidic catalyst comprises a molecular sieve with a one-dimensional pore system.

4. A process according to claim 3 wherein the molecular sieve is selected from the group consisting of SM-3, MAPO-11, SAPO-11, SSZ-32, ZSM-23, MAPO-39, SAPO-39, ZSM-22, SSZ-20, ZSM-35, SUZ-4, NU-23, NU-87, natural ferrierite and synthetic ferrierite.

5. A process according to claim 4 wherein the molecular sieve is SAPO-11 or SSZ-32.

6. A process according to claim 4 wherein the molecular sieve contains a Group VIII metal or mixture of Group VIII metals.

7. A process according to claim 5 wherein the molecular sieve contains a Group VIII metal or mixture of Group VIII metals.

8. A process according to claim 6 wherein the Group VIII metal is platinum, palladium or mixtures thereof.

9. A process according to claim 7 wherein the Group VIII metal is platinum, palladium or mixtures thereof.

10. A process according to claim 1 wherein the isomerized normal alpha-olefins have from about 20 to about 28 carbon atoms.

11. A process according to claim 1 wherein at least about 90% of the isomerized olefins are branched-chain olefins.

12. A process according to claim 1 wherein the hydroxyl-containing aromatic compound is selected from the group consisting of phenol, catechol, anisole, cresol, resorcinol and mixtures thereof.

13. A process according to claim 1 wherein the second solid, acidic catalyst comprises a sulfonic acid anionic ion exchange resin.

14. A process according to claim 1 wherein the second solid, acidic catalyst comprises an acidic clay.

15. A process for producing an alkylated hydroxyl-containing aromatic compound, said process comprising:
  (a) isomerizing a normal alpha-olefin or mixture of normal alpha-olefins having from about 16 to about 30 carbon atoms in the presence of a first acidic catalyst capable of inducing both olefin isomerization and skeletal isomerization to produce a mixture of isomerized olefins wherein at least about 70% of the isomerized olefins are branched-chain olefins;
  (b) alkylating a hydroxyl-containing aromatic compound selected from the group consisting of phenol, catechol, anisole, cresol, resorcinol and mixtures thereof, with said mixture of isomerized olefins in the presence of a second solid, acidic catalyst comprising a sulfonic acid resin catalyst or an acidic clay to thereby provide an alkylated hydroxyl containing aromatic compound having at least 82% of the para isomer.

16. A process according to claim 15 wherein the first acidic catalyst is a solid catalyst comprising at least one metal oxide, and having an average pore size of less than 5.5 angstroms, and wherein the isomerized olefin is a mixture of straight-chain and branched-chain olefins.

17. A process according to claim 16 wherein the first solid, acidic catalyst comprises a molecular sieve with a one-dimensional pore system.

18. A process according to claim 15 wherein the first acidic catalyst is a solid, acidic catalyst selected from the group consisting of SM-3, MAPO-11, SAPO-11, SSZ-32, ZSM-23, MAPO-39, SAPO-39, ZSM-22, SSZ-20, ZSM-35, SUZ-4, NU-23, NU-87, natural ferrierite and synthetic ferrierite.

19. A process according to claim 18 wherein the catalyst is SAPO-11 or SSZ-32.

20. A process according to claim 18 wherein the molecular sieve contains a Group VIII metal or mixture of Group VIII metals.

21. A process according to claim 19 wherein the molecular sieve contains a Group VIII metal or mixture of Group VIII metals.

22. A process according to claim 20 wherein the Group VIII metal is platinum, palladium or mixtures thereof.

23. A process according to claim 21 wherein the Group VIII metal is platinum, palladium or mixtures thereof.

24. A process according to claim 15 wherein the isomerized normal alpha-olefins have from about 20 to about 28 carbon atoms.

25. A process according to claim 15 wherein at least about 90% of the isomerized-olefins are branched-chain olefins.

26. A process according to claim 15 wherein the second solid, acidic catalyst comprises a sulfonic acid anionic ion exchange resin.

27. A process according to claim 15 wherein the second solid, acidic catalyst comprises an acidic clay.

* * * * *